(12) United States Patent
Rao et al.

(10) Patent No.: US 7,855,200 B2
(45) Date of Patent: Dec. 21, 2010

(54) METHOD FOR TREATMENT OF GASTRIC ULCERS AND ULCERS INDUCED BY ASPIRIN

(75) Inventors: Janaswamy Madusudana Rao, Andhra Pradesh (IN); Suresh Babu Katragadda, Andhra Pradesh (IN); Hari Babu Tatipaka, Andhra Pradesh (IN); Manjulatha Khanapur, Andhra Pradesh (IN); Muralidhar Gurachar Purohit, Andhra Pradesh (IN); Venkata Srinivas Pullela, Andhra Pradesh (IN); Jhillu Singh Yadav, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 395 days.

(21) Appl. No.: 11/651,106

(22) Filed: Jan. 9, 2007

(65) Prior Publication Data

US 2007/0213281 A1    Sep. 13, 2007

(30) Foreign Application Priority Data

Jan. 9, 2006    (IN) .............................. 74/DEL/2006

(51) Int. Cl.
| | |
|---|---|
| A61K 31/35 | (2006.01) |
| A61K 31/453 | (2006.01) |
| A61K 31/496 | (2006.01) |
| A61K 31/5377 | (2006.01) |

(52) U.S. Cl. .............................. 514/233.5; 514/254.11; 514/320; 514/456

(58) Field of Classification Search ....................... None
See application file for complete search history.

(56) References Cited

U.S. PATENT DOCUMENTS

| | | |
|---|---|---|
| 3,155,579 A | 11/1964 | Perrault |
| 5,399,584 A | 3/1995 | Ares et al. |
| 5,464,620 A | 11/1995 | Zhao |

FOREIGN PATENT DOCUMENTS

| | | |
|---|---|---|
| WO | WO 98/04541 | 2/1998 |
| WO | WO 2004/089392 A1 | 10/2004 |
| WO | WO 2005/011671 A1 | 2/2005 |

OTHER PUBLICATIONS

International Search Report and Written Opinion, Jun. 8, 2007.
K. Suresh Babu et al, Bioorg. Med. Chem. Lett. 15 (2005) 3953-3956, "Synthesis and in vitro study of novel 7-O-acyl derivatives of Oroxylin A as antibacterial agents.".
K. Suresh Babu et al, Bioorg. Med. Chem. Lett. 16 (2006) 221-224, "Synthesis and biological evaluation of novel C (7) modified chrysin analogues as antibacterial agents."
L. J. Chen et al, J. Chromatogr. A 988 (2003) 95-105, "Isolation and identification of four flavonoid constituents from the seeds of *Oroxylum indicum* by high-speed counter-current chromatopraphy.".
L. J. Chen et al, J. Chromatogr. A 1063 (2005) 241-245, "Comparison of high-speed counter-current chromatography instruments for the separation of the extracts of the seeds of *Oroxylum indicum*."
G. Flamini et al, Phytochemistry 61 (2002) 433-437, "Flavonoid glycosides from *Centaurea pseudoscabiosa* subsp. *pseudoscabiosa* from Turkey.".
F. Tombola et al, FEBS Letters 543 (2003) 184-189, "Plant polyphenols inhibit VacA, a toxin secreted by the gastric pathogen *Helicobacter pylori*."
M. Khandhar et al, Pharmaceutical Biology (2006) vol. 44, No. 5, 363-370, "Antiulcer Activity of the Root Bark of *Oroxylum indicum* Against Experimental Gastric Ulcers."

*Primary Examiner*—Phyllis G. Spivack
(74) *Attorney, Agent, or Firm*—Nixon & Vanderhye, P.C.

(57) ABSTRACT

The present invention relates to methods of using *Oroxylum indicum* as a rich source for flavanoid compounds having mucoprotective and antigastric ulcer properties, and containing Oroxylin A, Chrysin and Baicalein.

13 Claims, No Drawings

METHOD FOR TREATMENT OF GASTRIC ULCERS AND ULCERS INDUCED BY ASPIRIN

This application is a new U.S. utility application claiming benefit of IN 74/DEL/2006, dated 9 Jan. 2006, the entire content of which is hereby incorporated by reference.

This invention relates to identification of *Oroxylum indicum*, Indian medicinal plant as a rich source for flavanoid compounds. We have identified mucoprotective and antigastric ulcer properties in the flavone class of compounds. The invention also provides a flavanoids mixture obtained in substantial yield from hexane and acetone extracts. The hexane extract was fractionated, purified and the compounds identified as Oroxylin A, Chrysin and Baicalein. The acetone extract was purified and the compounds identified as methoxy chrysin, Oroxyloside methyl ester and chrysin-7-O-methyl glycoside. Invention of potent antigastric-ulcer compounds were accompanied with synthesis of few analogues derived from the oroxylin and chrysin, which were isolated from this plant in good yields. As per the results, oroxyloside methyl ester compound showed potent activity against gastric ulcers induced by aspirin, ethanol, stress and pylorus ligation.

Gastric or peptic ulcer constitutes a major disease that affects human gastrointestinal tract and major health problem both in terms of morbidity and mortality. The common clinical features of peptic ulcers are hyperacid secretion and ulcer formation in the stomach and duodenal part of the intestine. Peptic ulcer disease (PUD) primarily effects the adult population in developed and developing countries. The risk for peptic ulcer was highest in generations born before the turn of the century and has declined in all subsequent generations. Low family income, old age, smoking lower educational attainment, ethnicity, increased gastric acid output, *Helicobacter pylon*, NSAIDs and stress are that act as significant and independent basic risk factors in PUD risk factor. The prevalence of upper GI diseases is increasing in subjects aged 65 years and over. Almost 40% of GU (gastric ulcer) and 25% of DU (duodenal ulcer) in the elderly patients are associated with the use of non-steroidal anti-inflammatory drugs (NSAIDs). Gastrointestinal (GI) side effects include ulcers (found at endoscopy in 15-30% of patients using NSAIDs regularly), complications such as upper GI bleeding (annual incidence of 1.0-1.5%) and development of upper GI symptoms such as dyspepsia (occurring in up to 60% patients taking NSAIDs). NSAIDs are among most widely used prescribed drugs world wide for anti-inflammatory, analgesic and antipyretic effects, whereas low dose aspirin (also a NSAID) is used for cardiovascular prophylaxis. Although the therapeutic benefits of these drugs are substantial, their use is limited by their gastroduodenal toxicity, some of which can be serious or even fatal. Established risk factors for NSAIDs induced GI complications are age, ulcer history, heavy alcohol consumption, individual NSAIDs, dose association with corticoid or aspirin or anticoagulant (ulcer heamorrhage). The therapeutical acquisition of PUD of the year 2004 is the use of COX-2 inhibitors reduced significantly the GI side effects of anti-inflammatory treatments. Since cardiac adverse effects of certain COX-2 inhibitors (NSAIDs) had been reported, the treatments with COX-2 inhibitors came widely into question. Aspirin is a very useful medication for the prevention of cardiovascular thrombotic events in patients with or those at risk for cardiovascular disease (CVD). Patients being treated with aspirin, even at 81 mg/day for cardioprotection, should be assessed for factors that increase the risk for GI injury.

Stress has wide spread effects on various body systems. Stress has long been implicated as one of the risk factors for coronary diseases. Stress, defined as an acute threat to homeostasis, evokes an adaptive or allostatic response and can have both a short and long term influence on the function of the gastrointestinal tract. Stress ulceration of the stomach is associated with clinical conditions like trauma, head injury, burns, shock, sepsis and neurological disorders; and is now regarded as a multifactorial phenomenon. It is reported to result from interaction between mucosal, vascular and neurohumoral factors and the autonomic nervous system plays a crucial role. Circulatory disturbances and the nutritional deficiency are thus induced in the local tissue, which are then followed by a rapid appearance of a deep ulcer.

Gastrointestinal complications frequently occur in patients admitted to the intensive care unit. Of this ulceration and bleeding related to stress-related mucosal disease can lengthen hospitalization and increases mortality. The prophylactic regimen chosen to prevent stress ulcer bleeding should take into account the risk factors and underlying disease state of individual patients to provide the best therapy to those most likely to benefit.

Ethanol is common cause of acute gastric mucosal injury in both human and animals. This gastritis may produce life-threatening hemorrhage that requires surgical intervention. The mortality rate of such an intervention is at least 30%. In the rat persistence of gastric mucosal ischemia produces chronic ulceration of the stomach. Several other factors are associated with ulcer formation although this may be an indirect relationship such factors include hereditary, smoking, elevated calcium level, corticosteroids in high dose.

The majority of peptic ulcers causing growing burning or aching pain in the region of the stomach made worse by or unrelated to food. Pain tends to be worse at night and occurs usually 1 to 3 hours after food during the day. Additionally there may be food aversion, weight loss, nausea, belching or bloating. There is great individual variation and occasionally the pain may be referred to the back or the upper quadrant of the abdomen. Complications include bleeding, obstruction, perforation or intractable pain. Prophylactic options for patients suffering with gastrointestinal ulceration include antacids, sucralfate, histamine2-receptor antagonists (H2RAs), prostaglandins, muscarinic M1-antagonists and proton pump inhibitors. Therapy has been and still is largely empirical.

The prostaglandin's fulfilled their early promise and muscarinic $M_1$-antagonists, although more selective than the earlier anti-cholinergic agents, have limited application. Inhibition of the $H^+/K^+$ ATPase by non-competitive agents is limited to short-term administration and the development of a potent selective gastrin antagonist is yet be realized.

Reduction of symptoms, nullifying the side effects and improvement in quality of life are among the top priorities of diseases for the suffering persons. Although these factors need to be considered and balanced in evaluating new therapies for widespread use. The reduction in risk in a specific patient population should be considered before a particular regimen is deemed ineffective or too costly.

The plants create unexpected and novel structure to protect themselves from predator organism. By trail and error, several plants and plant products are identified as drugs. Natural product drugs although are highly effective and free from toxic side effects, have a disadvantage with respect to short supply and chemical structure, which makes their manufacture difficult or impossible. Natural product drugs have been a source of lead structure in drug design and development. Semi synthetic analogues or synthetic analogues closely related to the natural product drug of lead are synthesized and screened to disorder their action. In the light of above descriptions, in our isolation work flavonoids have been isolated which are potent antiulcer agents increasing the gastric pH, mucosal lining of stomach and related disorders, led to the identification of *Oroxylum indicum*, which contained in substantial yields potent antiulcer flavonoids for the first time.

*Oroxylum indicum* Vent has been advocated in traditional medical practice of India for several diseases. In folklore medicine in India, the powdered stem bark is used to treat dysentery, diarrhea, sore throat, cough and bone fractures (Kausik, P and Dhaman A. K, The medicinal plants and crude drugs of India, 2000, 398).

The main object of the invention is to examine and assess the relation between plant-originated substances and their bioactivity measured in terms of cytoprotective and antigastric ulceric activities and to determinate if these effects are capable of affecting the gastric mucosal lesions induced by absolute ethanol, cold stress, aspirin and pylorus ligated.

Another object of the invention is to assign new activity as anti ulcer compounds Oroxylin A, Chrysin, Baicalein, methoxy chrysin, Oroxyloside methyl ester and chrysin-7-O-methyl glucoside, isolated form either hexane extract or the acetone extract of *Oroxylum indicum* and synthetic analogues form Oroxylin A and chrysin. Further, these isolated and synthetic compounds are used for therapeutically for control of ulcer and other like diseases.

The present invention also relates to activity of these compounds and oroxyloside methyl ester (new compound) and another two compounds namely methoxy chrysin and chrysin-7-O-methyl glucoside as first time isolated form this plant *Oroxylum indicum*. All synthetic analogues prepared in the present invention is also new synthetic compounds. This invention further identified a first time anti ulcer activity using these compounds In accordance with the objects of this invention the present invention identified a new source namely *Oroxylum indicum* dried stem bark possessing substantial yields and compounds have the activity against gastric ulcer. This invention identifies presence of isolated compounds Oroxylin A, Chrysin, Baicalein, methoxy chrysin, Oroxyloside methyl ester and chrysin-7-O-methyl glucoside and synthetic analogs of oroxylin-A as a acyl ester derivatives and alkyl amino derivatives of chrysin.

The present invention also identifies for the first time oroxyloside methyl ester as new naturally occurring compound from acetone extract of *Oroxylum indicum*.

In another embodiment of the invention compound methoxy chrysin is isolated for the first time from acetone extract of *Oroxylum indicum*.

Still another embodiment of the present invention provides process for the isolation of Oroxylin A, Chrysin, Baicalein, methoxy chrysin, Oroxyloside methyl ester and chrysin-7-O-methyl glycoside as anti ulcer compounds form *Oroxylum indicum* the said process comprised following steps (1) hexane extract, (2) acetone extract.

a) extraction of dried stem bark of *Oroxylum indicum* with hexane by using Soxhlet apparatus
b) extract was filtered to afford solid separate out
c) subjecting the residue to a first elution with 1% methanol in chloroform to obtain Oroxylin A and
d) subjecting the residue (step c) to a second elution with 2% methanol in chloroform to obtain Chrysin and
e) subjecting the residue (step d) to a third elution with 3% methanol in chloroform to obtain Baicalein A further object of the invention relates to the isolation of these three compounds namely Oroxylin-A, Chrysin and Baicalein from *Oroxylum indicum* with hexane extract.

Further more all these compounds isolated from *Oroxylum indicum* shows anti-ulcer activity for the first time.

Further more extraction of dried stem bark of *Oroxylum indicum* with acetone, and process for isolation of compounds along with Oroxylin A, Chrysin and Baicalein, compounds Methoxy chrysin and Oroxyloside methyl ester and chrysin-7-O-methyl glycoside the said process comprising steps of a) subsequent extraction with acetone of the hexane extracted material by the same procedure to obtain the residue
b) subjecting the residue to a first elution with 1% methanol in chloroform to obtain Oroxylin A and
c) subjecting the residue (step b) to a second elution with 2% methanol in chloroform to obtain Chrysin and
d) subjecting the residue (step c) to a third elution with 3% methanol in chloroform to obtain Baicalein
e) subjecting the residue (step d) to fourth elution with 4% methanol in chloroform to obtain Methoxy chrysin
f) subjecting the residue (step e) to a fifth elution with 5% methanol in chloroform to obtain Oroxyloside methyl ester
g) subjecting the residue (step f) to a sixth elution with 7% methanol in chloroform to obtain chrysin-7-O-methyl glycoside.

Further invention identifies that in above said process compound Oroxyloside methyl ester was identified as first isolated natural compound and compounds methoxy chrysin and chrysin-7-O-methyl glycoside identified as a first time isolated compounds form this plant *Oroxylum indicum*, and the compound Oroxyloside methyl ester shows excellent potent molecule for the antiulcer activity and compound chrysin-7-O-methyl glycoside shows very good activity against gastric ulcer.

Present invention relates to the identification of isolation of potent antiulcer molecules from extracts of *Oroxylum indicum*, which may find preventive as well as therapeutic applications for the control of gastrointestinal toxicity along with other complications further use in disorders where gastrointestinal toxicity inhibition play an important role in prevention and treatment of diseases not mentioned in this description.

The present invention relies on the identification of *Oroxylum indicum* an Indian medicinal plant as possessing potent where gastrointestinal toxicity inhibitors. The hexane extract of dried stem bark of *Oroxylum indicum* constitutes 95% of three major active principles identified as Oroxylin A, Chrysin, Baicalein and acetone extract contains six major active principles, that contains apart from Oroxylin A, Chrysin, Baicalein and compounds namely methoxy chrysin, Oroxyloside methyl ester and chrysin-7-o methyl glycoside and synthesized analogues of Oroxylin, Chrysin in substantial yields. These mixtures and molecules may find preventive as well as therapeutic application in controlling disorders of gastrointestinal disorders and diseases.

These antigastric ulcer molecule(s) may be administrated by any suitable conventional method prevalent in pharmaceutical practice for the treatment of gastrointestinal toxicity, control gastric pH and reduction ulcers risk factors in GI toxicity, and also in disease condition such as inflammation, stress conditions, NSAID therapy requiring inhibition of gastric acid output, formation of mucosal lining, elevate the gastric acid pH for prevention and treatment of diseases mentioned and not mentioned in this invention.

The potent antiulcer OA-5 molecule in this invention antagonize the aggressive factors, which play in the pathogenesis of gastric lesions and augment defensive factors to protect the gastric mucosal from injury. Application as the case of antigastric ulcer molecules may preferably be taken orally and potentiate the mechanism of action and hence impart better therapeutic action. The antigastric ulcer molecules present in pharmaceutical preparation in this invention may be formulated with any of the suitable pharmaceutically acceptable additive, carrier, vehicle, food preparations etc., suitable for human application. The materials should be selected such that they should not interfere with the potency and the property of the mixture or the molecule but materials that can add to or improve the activity, are preferred and can decided by the conventional art and the skills available in formulary.

Effective Dose:

Effective dose level and duration of drug administration may be decided by the skill of ordinary art in order to bring therapeutic parameter of the disease under consideration under the control. The actual rate, amount of applications, and the time of administration may vary depending upon the disease condition and severity and may be irrespective of the concentration and duration as described in the examples of this invention.

Synthesis of 7-O-acyl Derivatives of Oroxylin A:

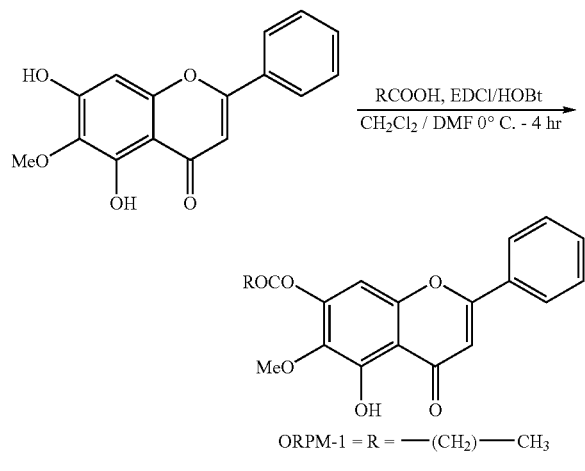

ORPM-1 = R = —(CH$_2$)—CH$_3$
ORC-16 = R = —(P-Me)-Phenyl

Procedure: The corresponding acid, EDCl (0.836 mmol) and HOBt (0.69 mmol) were cooled to 0° C. and stirred in anhydrous methylene chloride (5 ml) for 15-30 min under nitrogen atmosphere. To this mixture, Oroxylin A (0.704 mmol) in anhydrous N, N-dimethylformaldehye (3 ml) was added. The entire reaction mixture was stirred at room temperature for 4-5 h under nitrogen. After completion of the reaction (TLC), the reaction mixture was poured into ice water and washed with methylene chloride (2×10 ml). The combined organic layers were dried over anhydrous sodium sulphate and concentrated under vacuum. Residue was purified by column chromatography on silica gel (60-120 mesh) to give corresponding 7-O-acyl derivatives of Oroxylin A ORPM-1 and ORC-16 in good yields.

Preparation of Alkyl Amino Derivatives of Chrysin:

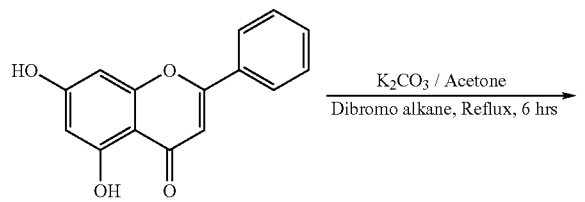

-continued

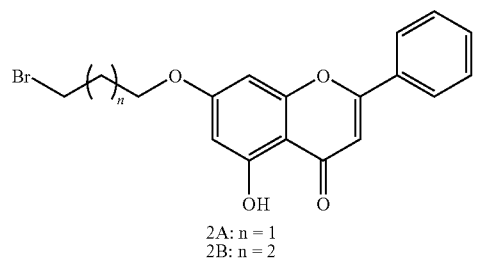

2A: n = 1
2B: n = 2

2 $\xrightarrow{R, K_2CO_3/CH_3CN}$ Reflux, 3-4 hrs

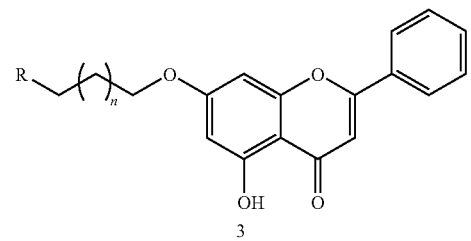

3

3a- CHM-2 = R = Morpholine
3b- NMC-2 = R = N-Methyl Piperzine
3c- CHM-2 = R = N,N-Dimethyl amine
3d- CHM-2 = R = Piperdine
3e- CHM-3 = R = Morpholine
3f- NMC-3 = R = N-Methyl Piperzine General Procedure for the Preparation of 7-O-Alkylamino Derivatives of Chrysin:

i) General Procedure for the Preparation of 7-O-Alkyl Derivatives of Chrysin:

To a mixture of chrysin 1 (1 g, 3.93 mmol) and anhydrous potassium carbonate (0.81 g, 5.8 mmol) in 20 ml acetone, corresponding dibromoalkane (1,3-dibromo propane for 2a, 1,4-dibromo butane for 2b. The mixture was refluxed under nitrogen atmosphere for 3-4 h. After completion of the reaction potassium carbonate was filtered and washed with excess of acetone (2×50 ml). The combined acetone layers are concentrated under vacuum. The residue was purified by column chromatography on silica gel (60-120 mesh) to yield 7-O-bromoalkyl chrysin (2a, 2b) in pure form.

ii) General Procedure for the Preparation of 7-O-Alkyl Amino Derivatives of Chrysin:

To a mixture of bromoalkyl chrysin (2a, 2b) and anhydrous potassium carbonate (2.41 g, 17.2 mmol) in 20 ml acetonitrile, corresponding amine was added. The mixture was refluxed under nitrogen atmosphere for 3-4 h. After completion of the reaction, the reaction mixture was brought to room temperature and was poured into ice water and washed with methylene chloride (2×10 ml). The combined organic layers were dried over anhydrous sodium sulphate and concentrated under vacuum. The residue was purified by column chromatography on silica gel (60-120 mesh) to give the corresponding 7-O-alkylaminoderivatives of chrysin in very good yields (60-80%).

Preparation Glycoside Derivatives of Flavanoids:

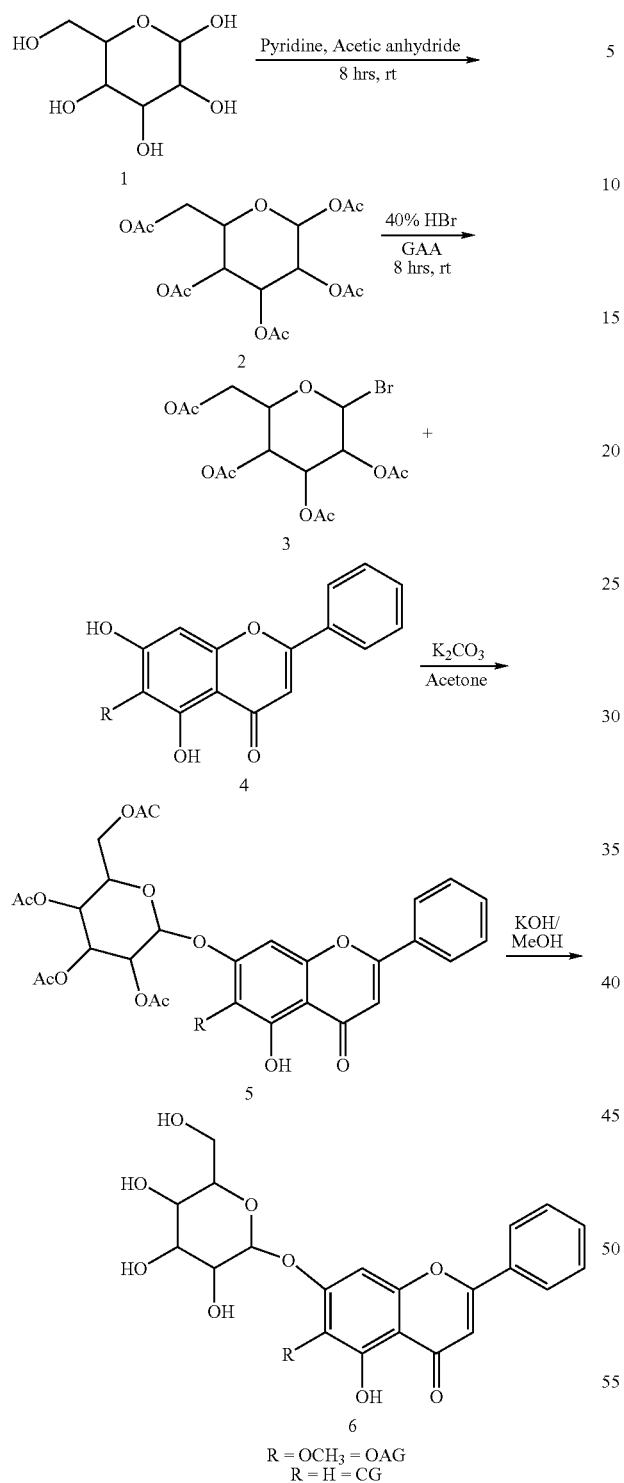

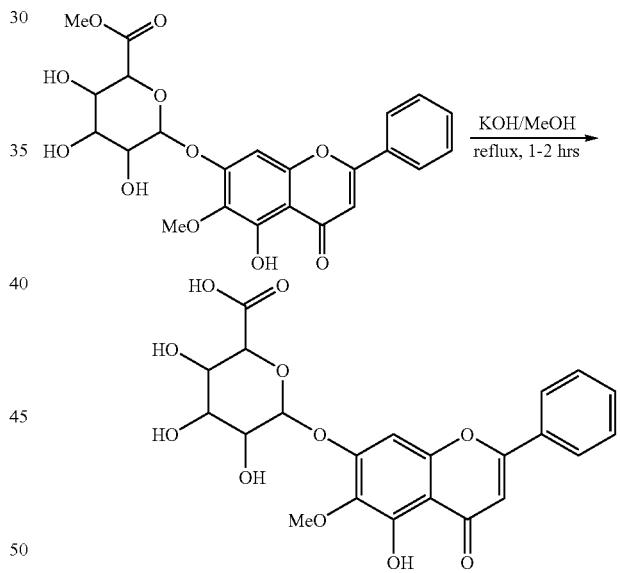

Procedure: 1) Acetic anhydride (2.5 ml) was added to a solution of anhydrous D-glucose (1.0 g, 5.55 mmol) in 5 ml of pyridine and stirred at RT for 8 hrs. The solution was evaporated in vacuo, the syrupy residue dissolved in 25 ml of $CHCl_3$ and washed with water, saturated $Na_2SO_4$ and evaporated in vacuo gives 2,3,4,6 penta-O-acyl-D-galacto pyronose (2) with out further purification the yield is 92%.

2). A solution of Hydrogen bromide in glacial acetic acid (40%, 5 ml) was added to a stirred solution of (2) (1.17 g, 3.0 mmol) in 10 ml of acetic acid. Stirring was continued at RT for 8 hrs, kept away form direct sunlight. The reaction mixture is carefully poured in to 50 ml of ice water and extracted with three times with $CHCl_3$. The combine layers are washed with saturated $Na_2SO_4$ solution and NaCl solution and evaporated in vaccuo and this yellow syrupy residue is dissolved in 5 ml of ether and allowed to crystallize at 5° C. and resultant compound was gives the aceto bromo galactose (3) yield was 72%.

3). Take the corresponding flavonoid (2.43 mmol) dissolved in acetone and add anhydrous $K_2CO_3$ (0.4 g, 2.916 mmol) and stirrer for 15 min then add acetobromogalactose (3) (1 g, 2.43 mmol) and stirrer at RT for 3-4 hrs. After completion of reaction filter the reaction mixture and evaporated in vacuo, purify with column chromatography and yielded 5a and 5b 85-90%.

4) To a solution of 5a and 5b in methanol add methanolic KOH and stirred for 1-2 hrs and after completion of reaction, evaporate the methanol completely dissolved the reaction mixture in water and extracted with $CHCl_3$ two times and combine layers dried over $Na_2SO_4$ and evaporated in vacuo gives 6a and 6b in pure form without further purification. Yield 95%.

6). Preparation of OA-5 Acid (7-O-Glucoronide Derivative of Oroxylin A):

Procedure: Compound dissolved in methanolic KOH and reflux for 1-2 hrs. After completion of reaction (monitored by TLC), methanol completely dissolved the reaction mixture in water and extracted with ethyl acetate two times and combine layers dried over $Na_2SO_4$ and evaporated in vacuo gives corresponding acid on column chromotogarphy, Yield: 85%.

In the following structures,

FIG. 1 represents formula of Oroxylin-A [5,7-Dihydroxy-6-methoxy-2-phenylchromen-4-one]

FIG. 2 represents formula of Chrysin [5,7-dihydroxy-2-phenyl-chromen-4-one]

FIG. 3 represents formula of Baicalein [5,6,7-trihydroxy-2-phenyl-chromen-4-one]

FIG. 4 represents formula of Methoxy chrysin [5-hydroxy-7-methoxy-2-phenyl-chromen-4-one]

FIG. 5 represents formula of Oroxoloside methyl ester [3,4,5-trihydroxy-6-(6-methoxy-4-oxo-2-phenyl-4-H-chromen-7-yoloxy) tetrahydro-pyran-2-carboxylicacid methyl ester]

FIG. 6 represents formula of chrysin-7-O-methyl glycoside [3,4,5-trihydroxy-6-(4-oxo-2-phenyl-4-H-chromen-7-yoloxy) tetrahydro-pyran-2-carboxylicacid methyl ester]

FIG. 7 represents formula of ORC-16 [Heptadecanoic acid 5-hydroxy-6-methoxy-4-oxo-2-phenyl-4H-chromen-7-yl ester]

FIG. 8 represents formula of ORPM-1 [4-methyl-benzoic acid 5-hydroxy-6-methoxy-4-oxo-2-phenyl-4-H-chromen-7-yl ester]

FIG. 9 represents formula CPP-2 [5-Hydroxy-2-phenyl-7-(3-piperidin-1-yl-propoxy)-chromen-4-one]

FIG. 10 represents formula of CHM-2 [5-Hydroxy-7-(3-morpholin-4-yl-propoxy)-2-phenyl chromen-4-one]

FIG. 11 represents formula of CHN-2 [7-(3-Dimethyl amino-propoxy)-5-hydroxy-2-phenyl chromen-4-one]

FIG. 12 represents formula of NMC-2 [5-Hydroxy-7-[3-(4-methyl-piperzin-1-yl]-propoxy)-2-phenyl hromen-4-one]

FIG. 13 represents formula of NMC-3 [5-Hydroxy-7-[4-(4-methyl-piperzin-1-yl]-butoxy)-2-phenyl chromen-4-one]

FIG. 14 represents formula of CHM-3 [5-Hydroxy-7-(4-morpholin-4-yl-butoxy)-2-phenyl chromen-4-one]

FIG. 15 represents formula of OAG [5-Hydroxy-6-methoxy-2-phenyl-7-(3,4,5-trihydroxy-6-hydroxyrnethyl-tetrahydro-pyran-2-yloxy)-chromen-4-one]

FIG. 16 represents formula of CG [5-Hydroxy-2-phenyl-7-(3,4,5-trihydroxy-6-hydroxymethyl-tetrahydro-pyran-2-yloxy)-chromen-4-one]

FIG. 17 represents formula of OA-5 Acid [3,4,5-Trihydroxy-6-(5-hydroxy-6-methoxy-4-oxo-2-phenyl-4H-chromen-7-yloxy)-tetrahydro-pyran-2-carboxylic acid].

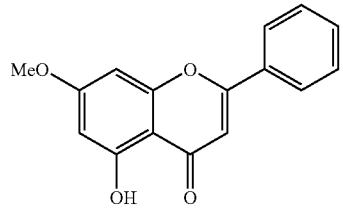

FIG.: 1

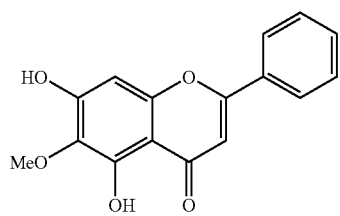

FIG.: 2

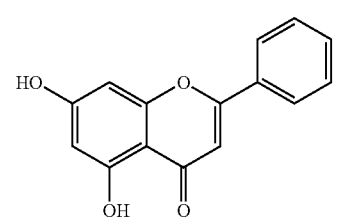

FIG.: 3

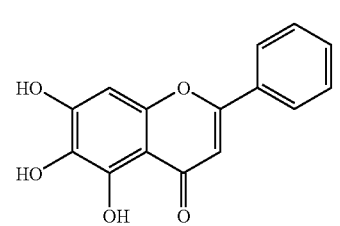

-continued

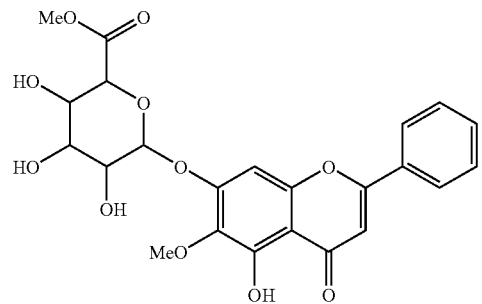

FIG.: 4

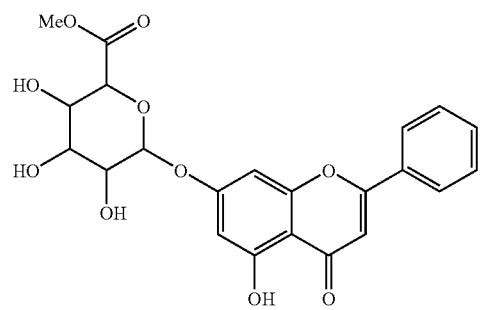

FIG.: 5

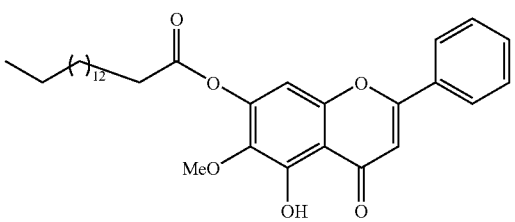

FIG.: 6

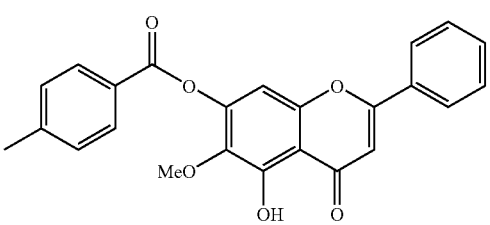

FIG.: 7

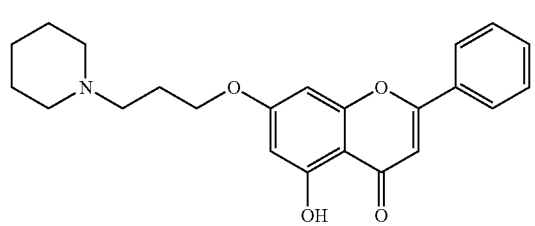

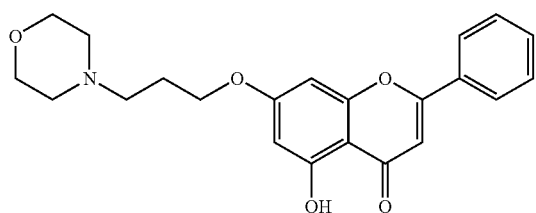
FIG.: 10

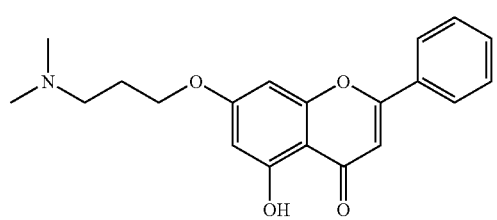
FIG.: 11

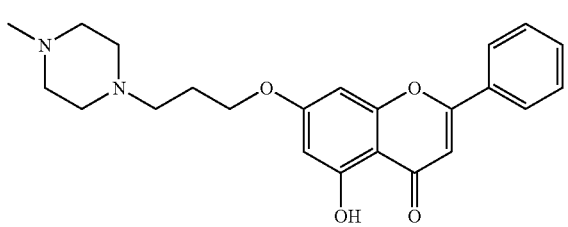
FIG.: 12

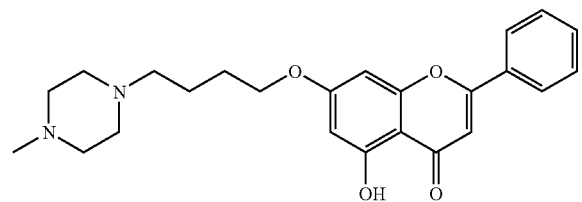
FIG.: 13

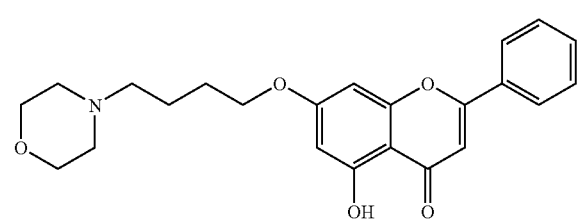
FIG.: 14

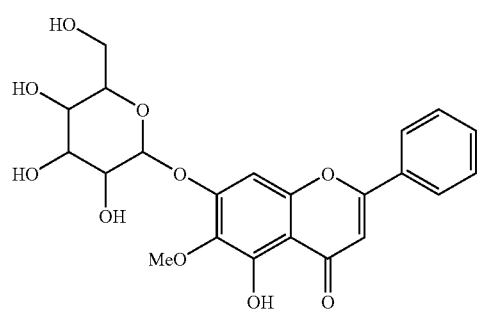
FIG.: 15

-continued

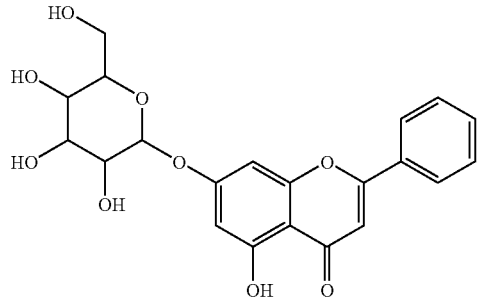
FIG.: 16

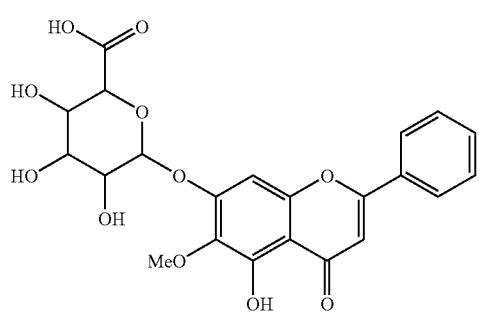
FIG.: 17

In another embodiment of the invention of Oroxylin A (FIG. 1) obtained from *Oroxylum indicum* has the following spectrochemical and physical properties MP:231-232° C. IR (KBr)$v_{max}$ 3435, 2825, 1622, 1016 cm$^{-1}$. $^1$H NMR (200 MHz, CDCl$_3$+MeOH-d$_4$) (δ) 7.82-7.86 (2H, m, H-2', 6'), 7.42-7.56 (3H, m, H-3', 4', 5'), 6.62 (1H, s, H-8), 6.58 (1H, s, H-3), 3.96 (3H, s, Ar—OMe). $^{13}$C NMR (50 MHz, DMSO d$_6$) δ163.37 (C-2), 104.46 (C-3), 182.31 (C-4), 152.64 (C-5), 130.80 (C-6), 157.62 (C-7), 94.49 (C-8), 152.79 (C-9), 104.71 (C-10), 131.60 (C-1'), 126.42 (C-2'), 129.20 (C-3'), 132.06 (C-4'), 60.06 (OMe). EIMS:284 (M$_+$, 100).

In another embodiment of the invention of Chrysin (FIG. 2) obtained from *Oroxylum indicum* has the following spectralchemical and physical properties MP:285-286° C. IR (KBr)$v_{max}$ 3450, 2925, 1626, 1024 cm$^{-1}$. $^1$H NMR (400 MHz, CDCl$_3$+MeOH-d$_4$) (δ) 7.82-7.92 (2H, m, H-2', 6'), 7.44-7.58 (3H, m, H-3', 4', 5'), 6.64 (1H, s, H-8), 6.44 (1H, s, H-3), 6.24 (1H, s, H-6). $^{13}$C NMR (50 MHz, DMSO d$_6$) δ163.0 (C-2), 105.0 (C-3), 181.6 (C-4), 161.5 (C-5), 99.0 (C-6), 164.3 (C-7), 94.0 (C-8), 157.3 (C-9), 104.0 (C-10), 138.7 (C-1'), 126.1 (C-2'), 128.8 (C-3'), 131.6 (C-4'), 128.8 (C-5'), 126.1 (C-6'). EIMS: M$^+$ 254.

In another embodiment of the invention of Baicalein (FIG. 3) obtained from *Oroxylum indicum* has the following spectral chemical and physical properties MP:223-226° C. $^1$H NMR (400 MHz, CDCl$_3$+MeOH-d$_4$) (δ) 7.82-7.98 (2H, m, H-2', 6'), 7.44-7.60 (3H, m, H-3', 4', 5'), 6.62 (1H, s, H-8), 6.58 (1H, s, H-3). $^{13}$C NMR (50 MHz, DMSO d$_6$) δ162.9 (C-2), 104.5 (C-3), 182.1 (C-4), 147.0 (C-5), 129.3 (C-6), 153.7 (C-7), 94.0 (C-8), 149.9 (C-9), 104.3 (C-10), 131.0 (C-1'), 126.2 (C-2'), 129.0 (C-3'), 131.7 (C-4'), 129.0 (C-5'), 126.2 (C-6). EIMS:270 (M$^+$, 100).

In another embodiment of the invention of Methoxy chrysin (FIG. 4) obtained from *Oroxylum indicum* has the following spectralchemical and physical properties MP:164° C. (KBr) $v_{max}$ 3450, 2925, 1654, 1621, 1016 cm$^{-1}$. $^1$H NMR (200 MHz, CDCl$_3$) (δ)13.0 (1H, s, OH-5), 7.82-7.96 (2H, m, H-2', 6'), 7.44-7.60 (3H, m, H-3', 4', 5'), 6.62 (1H, s, H-8), 6.60 (1H, s, H-3), 6.58 (1H, s, H-6), 3.96 (3H, s, OMe). $^{13}$C NMR (300 MHz, CDCl$_3$) (δ)164.08 (C-2), 105.04 (C-3), 182.88 (C-4), 164.08 (C-5), 93.97 (C-6), 153.31 (C-7), 93.97 (C-8), 153.31 (C-9), 105.50 (C-10), 130.96 (C-1'), 126.24 (C-2'), 128.88 (C-3'), 131.26 (C-4'), 128.88 (C-5'), 126.24 (C-6'), 60.63 (Ar—OMe). EIMS:192 (M$^+$, 100).

In another embodiment of the invention of Oroxyloside methyl ester (FIG. 5) obtained from *Oroxylum indicum* has the following spectralchemical and physical properties MP:201° C. UV λ$_{max}$ (MeOH)345, 285 nm. IR (KBr) ν$_{max}$ 3395, 2924, 1735 (ester-C=O), 1618 (—C=O), 1461, 1359, 1224, 1076 cm$^{-1}$. $^1$H NMR (200 MHz, DMSO-d$_6$) (δ) 12.78 (1H, s, OH-5), 7.90-8.0 (2H, m, H-2', 6'), 7.48-7.60 (3H, m, H-3', 4', 5'), 6.84 (1H, s, H-8), 6.80 (1H, s, H-3), 3.4-5.50 (m, sugar protons), 3.78 (3H, s, OMe), 3.82 (3H, s, Ar—OMe). $^{13}$C NMR (300 MHz, DMSO-d$_6$) (δ) 163.72 (C-2), 104.95 (C-3), 182.37 (C-4), 152.52 (C-5), 132.04 (C-6), 156.08 (C-7), 94.07 (C-8), 152.17 (C-9), 106.12 (C-10), 130.59 (C-1'), 126.35 (C-2',6'), 129.03 (C-3',5'), 132.06 (C-4'), 99.49 (C-1"), 75.60 (C-2"), 75.25 (C-3"), 72.77 (C-4"), 71.18 (C-5"), 168.96 (C-6"), 60.21 (Ar—OMe), 51.81 (OMe). EIMS: 475 (M$^+$+1, 100).

In another embodiment of the invention of Chrysin-7-O-methyl glycoside (FIG. 6) obtained from *Oroxylum indicum* has the following spectralchemical and physical properties MP:201° C. UV λ$_{max}$ (MeOH)345, 285 nm. IR (KBr) ν$_{max}$ 3390, 2928, 1735 (ester-C=O), 1610 (—C=O), 1465, 1345, 1210, 1055 cm$^{-1}$. $^1$H NMR (200 MHz, DMSO-d$_6$) (δ) 12.70 (1H, s, OH-5), 7.92-8.05 (2H, m, H-2', 6'), 7.45-7.56 (3H, m, H-3', 4', 5'), 6.80 (1H, s, H-8), 6.74 (1H, s, H-6) 6.68 (1H, s, H-3), 3.4-5.50 (m, sugar protons), 3.70 (3H, s, OMe). $^{13}$C NMR (300 MHz, DMSO-d$_6$) (δ) 162.65 (C-2), 104.64 (C-3), 181.97 (C-4), 152.05 (C-5), 98.56 (C-6), 155.60 (C-7), 94.23 (C-8), 151.87 (C-9), 106.10 (C-10), 131.59 (C-1'), 126.05 (C-2',6'), 129.15 (C-3',5'), 132.00 (C-4'), 99.43 (C-1"), 75.45 (C-2"), 75.05 (C-3"), 72.54 (C-4"), 70.98 (C-5"), 168.90 (C-6"), 51.81 (OMe). EIMS: 445 (M$^+$+1)

In another embodiment of the invention of synthetic analogues from oroxylin-A obtained from *Oroxylum indicum* as acyl derivatives namely 7-O-dodecyl oroxylin A (FIG. 7) the following spectralchemical and physical properties MP:101.2° C.; $^1$H NMR (300 MHz, CDCl$_3$) δ 12.82 (1H, s, OH-5), 7.88-7.92 (2H, m, H-2', 6'), 7.50-7.56 (3H, m, H-3', 4', 5'), 6.70 (1H, s, H-8), 6.64 (1H, s, H-3), 3.90 (3H, s, OMe), 2.62 (2H, t, H-2"), 1.60-1.80 (2H, m, H-3"), 1.22-1.40 (16H, brs, H-4"-H-11"), 084 (3H, t, H-12"). FABMS: 467 (M$^+$+1).

In another embodiment of the invention of synthetic analogues from oroxylin-A obtained from *Oroxylum indicum* as acyl derivatives named 7-O-(p-methylbenzoyl) oroxylin A (FIG. 8) the following spectralchemical and physical properties MP: 203° C., $^1$H NMR (300 MHz, CDCl$_3$) δ 12.82 (1H, s, OH-5), 8.46 (2H, d, J=6Hz, H-2", 6"), 7.82-7.84 (2H, m, H-2', 6'), 7.50-7.58 (3H, m, H-3', 4', 5'), 7.36 (2H, d, J 6Hz, H-3", 5"), 6.90 (1H, s, H-8), 6.70 (1H, s, H-3), 3.96 (3H, s, OMe), 2.52 (3H, s, Ar-Me). FABMS: 429 (M$^+$+Na).

In another embodiment of the invention of synthetic analogues from chrysin obtained from *Oroxylum indicum* as alkyl amino derivatives 7-O-propyl (piperidinyl) Chrysin (FIG. 9) the following spectral-chemical and physical properties: MP: 215° C., $^1$H NMR (300 MHz, CDCl$_3$) δ 12.50 (1H, s, OH-5), 7.82-7.86 (2H, m, H-2', 6'), 7.44-7.58 (3H, m, H-3', 4', 5'), 6.66 (1H, s, H-8), 6.58 (1H, s, H-3), 6.39 (1H, s, H-6), 4.16 (2H, t, H-1"), 2.38-2.58 (6H, m, H-2''', 6''' and H-3'''), 1.98-2.08 (2H, m, H-2"), 1.58-1.60 (4H, m, H-3''', 5'''), 1.41-1.50 (2H, m, H-4'''). FABMS: 402 (M$^+$+Na).

In another embodiment of the invention of synthetic analogues from chrysin obtained from *Oroxylum indicum* as alkyl amino derivatives 7-O-propyl (morphinyl) chrysin (FIG. 10) the following spectralchemical and physical properties: MP:138° C., $^1$H NMR (400 MHz, CDCl$_3$) δ 12.60 (1H, s, OH-5), 7.86-7.90 (2H, m, H-2', 6'), 7.50-7.62 (3H, m, H-3', 4', 5'), 6.64 (1H, s, H-8), 6.46 (1H, s, H-3), 6.38 (1H, s, H-6), 4.18 (2H, t, H-1"), 3.82 (4H, t, H-3''', 5'''), 2.40-2.60 (6H, m, H-2''', 6''', H-3"), 1.9-2.10 (2H, m, H-2"). FABMS: 382 (M$^+$+1).

In another embodiment of the invention of synthetic analogues from chrysin obtained from *Oroxylum indicum* as alkyl amino derivatives 7-O-propyl (N, N-Dimethyl) chrysin (FIG. 11) the following spectralchemical and physical properties: MP 119-120° C., $^1$H NMR (400 MHz, CDCl$_3$) δ12.72 (1H, s, OH-5), 7.82-7.86 (2H, m, H-2', 6'), 7.50-7.58 (3H, m, H-3', 4', 5'), 6.64 (1H, s, H-8), 6.48 (1H, s, H-3), 6.38 (1H, s, H-6), 4.10 (2H, t, H-1"), 2.42 (2H, H-3"), 2.22 (6H, s, 2×Me), 1.98-2.02 (2H, m, H-2"). FABMS: 340 (M$^+$+1)

In another embodiment of the invention of synthetic analogues from chrysin obtained from *Oroxylum indicum* as alkyl amino derivatives 7-O-propyl (N-methyl piperizinyl) chrysin (FIG. 12) the following spectralchemical and physical properties: MP:128-130° C., $^1$H NMR (400 MHz, CDCl$_3$) δ 12.70 (1H, s, OH-5), 7.84-7.86 (2H, m, H-2', 6'), 7.46-7.58 (3H, m, H-3', 4', 5'), 6.64 (1H, s, H-8), 6.52 (1H, s, H-3), 6.18 (1H, s, H-6), 4.12 (2H, t, H-1"), 2.40-2.60 (9H, m, H-3''', 5''', H-3" and H-2''', 6'''), 2.30 (3H, s, Me), 1.90-2.10 (2H, m, H-2"). FABMS: 395 (M$^+$+1).

In another embodiment of the invention of synthetic analogues from chrysin obtained from *Oroxylum indicum* as alkyl amino derivatives 7-O-butyl (N-methyl piperizinyl) chrysin (FIG. 13) the following spectralchemical and physical properties: MP:80° C., $^1$H NMR (300 MHz, CDCl$_3$) δ 12.64 (1H, s, OH-5), 7.76-7.86 (2H, m, H-2', 6'), 7.40-7.58 (3H, m, H-3', 4', 5'), 6.58 (1H, s, H-8), 6.40 (1H, s, H-3), 6.30 (1H, s, H-6), 4.0 (2H, t, H-1"), 2.80-3.0 (10H, m, H-2''', 6''', H-3''', 5''', H-4"), 2.58 (3H, s, Me), 1.6-1.82 (4H, m, H-2", 3"). FABMS: 431 (M$^+$+Na).

In another embodiment of the invention of synthetic analogues from chrysin obtained from *Oroxylum indicum* as alkyl amino derivatives 7-O-butyl (morphinyl) chrysin Chrysin (FIG. 14) the following spectralchemical and physical properties MP:130° C., $^1$H NMR (300 MHz, CDCl$_3$) δ 12.38 (1H, s, OH-5), 7.80-7.88 (2H, m, H-2', 6'), 7.50-7.58 (3H, m, H-3', 4', 5'), 6.72 (1H, s, H-8), 6.62 (1H, s, H-3), 6.40 (1H, s, H-6), 4.10 (2H, t, H-1"), 3.70-3.76 (4H, m, H-3''', 5'''), 2.40-2.50 (6H, m, H-2''', 6''', H-4"), 1.80-2.0 (2H, m, H-3"), 1.60-1.80 (2H, m, H-2"). FABMS: 396 (M$^+$+1).

In another embodiment of the invention of synthetic analogues from oroxylin A obtained from *Oroxylum indicum* as glycoside derivatives OAG (FIG. 15) the following spectralchemical and physical properties: $^1$H NMR (200 MHz, CDCl$_3$+MeOH-d$_4$) δ12.78 (1H, s, OH-5), 7.80-7.86 (2H, m, H-2', 6'), 7.42-7.56 (3H, m, H-3', 4', 5'), 6.83 (1H, s, H-8), 6.50 (1H, s, H-3), 3.4-5.50 (m, sugar protons), 3.78 (3H, s, OMe), 3.92-3.96 (2H, d).

In another embodiment of the invention of synthetic analogues from Chrysin obtained from *Oroxylum indicum* as glycoside derivatives CG (FIG. 16) the following spectralchemical and physical properties: $^1$H NMR (200 MHz, CDCl$_3$+MeOH-d$_4$) δ12.78 (1H, s, OH-5), 7.82-7.98 (2H, m, H-2', 6'), 7.44-7.60 (3H, m, H-3', 4', 5'), 6.63 (1H, s, H-8), 6.48 (1H, s, H-3), 6.24 (1H, s, H-6), 3.4-5.50 (m, sugar protons), 3.90-3.93 (2H, d).

In another embodiment of the invention of synthetic analogues from oroxyloside methyl ester obtained from *Oroxy-*

*lum indicum* as glycoside derivative OA-5 Acid (FIG. 17) the following spectralchemical and physical properties: $^1$H NMR (200 MHz, MeOH-d$_4$) (δ) 12.70 (1H, s, OH-5), 7.94-8.05 (2H, m, H-2', 6'), 7.40-7.55 (3H, m, H-3', 4', 5'), 6.80 (1H, s, H-8), 6.57 (1H, s, H-3), 3.4-5.50 (m, sugar protons), 3.82 (3H, s, Ar—OMe).

EXAMPLE 1

Experimental Protocol

Process of Isolation of Oroxylin A, Chrysin and Baicalein

The dried powdered stem bark (200 g) was first defatted with petrol in a soxlet apparatus. The bright yellow coloured powdered solid was obtained after the filtration of the hexane extract. The solid (2 g) was chromatographed over silica gel (60-120 mesh), 3.5 cm dia column loaded to a height of 60 cm. The column was successively eluted with 1% methanol in chloroform to afford Oroxylin-A. The yield of Oroxylin-A is around 1.2 g. Further elution of the column with 2% methanol in chloroform afforded chrysin. The yield of Chrysin is around 0.2 g. Further elution of the column with 3% methanol in chloroform afforded Baicalein. The yield of Baicalein is around 0.5 g.

Process of Isolation of Methoxy Chrysin, Oroxyloside Methyl Ester and Chrysin-7-O-Methyl Glycoside:

The dried powdered stem bark (200 g) was successively extracted with hexane and acetone. The acetone extract on evaporation afforded a dark brown colored residue (3 g). The residue was chromatographed over silica gel (60-120 mesh), 3.5 cm dia column loaded to a height 60 cm. In addition to oroxylin A, Chrysin and Baicalein two more compounds namely Methoxychrysin, Oroxyloside methyl ester and chrysin-7-O-methyl gluconide were isolated as follows. The column was successively eluted with 1% methanol in chloroform to afford Oroxylin-A. The yield of Oroxylin-A is around 0.2 g. Further elution of the column with 2% methanol in chloroform afforded chrysin. The yield of Chrysin is around 0.25 g. Further elution of the column with 3% methanol in chloroform afforded Baicalein. The yield of Baicalein is around 1.5 g. Further elution of the column successively with 4% methonal in chloroform afford Methoxy chrysin. The yield of methoxy chrysin is around 0.5 g. Further elution of the column with 5% methonal in chloroform afford Oroxyloside methyl ester. The yield of Oroxyloside methyl ester is around 0.4 g. Further evolution of the column with 7% methanol in chloroform afford chrysin-7-O-methyl gluconide. The yield of the chrysin-7-O-methyl gluconide is around 0.3 g. All the above compounds were isolated in 95% purity.

The spectrochemical and physical properties of the all above compounds are discussed earlier. Further all the synthetic analogues preparation and yields were discussed in earlier procedures.

EXAMPLE 2

Experimental Method for Gastric Ulcer

The compounds taken under study for antigastric ulcer screening by four different models were selected using experimental albino rats:
1. Aspirin induced gastric ulceration
2. Pylorus ligated gastric ulceration
3. Ethanol induced gastric ulceration
4. Stress induced gastric ulceration The commercially available drug ranitidine (sigma), Omeprazole (sigma) and sucralfate (Merck) were used as reference standard in experimental models. The Tween-80 (SD fine chemicals) was used as vehicle for the administration of the drug, which is used as control. The results obtained are presented in the following tables.

2.1 Acetyl Sailcylic Acid Induced Ulcer:

Antiulcer activity of the compounds under taken was studied. The animals were divided into 20 groups of 6 animals each. Group 1 received the vehicle Tween 80 (1%, 1 ml) which served as the control. Group 2 received ranitidine at a dose of 50-mg/kg body weight, which served as standard for comparison. Group 3 to 20 at a dose of 25 mg/kg body weight. Rats were administered per orally with a daily dose of the compounds and the drug ranitidine for a period of five days and then fasted for 24 hours. The narcotizing agent acetyl salicylic acid (aspirin) at a dose of 200 mg/kg body weight was administered as a suspension in tween-80 (1%), 30 min after the drug administration each day. All drugs were administered orally on the 6th day after the last administration of the drugs and the ulcer inducing agent aspirin, the rats were killed by cervical dislocation and their stomach were opened along the greater curvature and washed with luke warm saline and examined under a dissecting microscope. The ulcer index was calculated for each stomach. The results are given in table no. 1.

2.2 Cold Restraint Induced Ulcers

The antiulcer activity of the compounds was studied. The animals were divided into 21 groups of 7 animals each. Group 1 received the vehicle Tween 80 (1%, 1 ml) which served as the control. Group 2 received ranitidine at a dose of 50-mg/kg body weight, which served as standard for comparison. Group 3 to 21 at a dose of 25 mg/kg body weight. Animals were deprived of food 48 hours before the experiment. The water was allowed for free access. Rats were administered per orally with compounds and the drug ranitidine. The water was removed 1 hour before restraint and exposed to a temperature of 4° C. for 2 hours. Two hours after stress, the animals were sacrificed. The stressed animals were opened along the greater curvature and the severity of gastric ulcer was assessed in terms of mean ulcer index. Results are tabulated below in table no. 2.

2.3 Ethanol Induced Ulcers

The animals were divided into 22 groups of 6 animals each. Animals were deprived of food for 48 hours but had free access to water. Group 1 received the vehicle Tween 80 (1%, 1 ml) which served as the control. Group 2 received ranitidine at a dose of 50-mg/kg-body weight, which served as standard for comparison. Group 3 to received Omeprazole at a dose of 30-mg/kg body weight, which served as standard for comparison. Group 4 received sucralfate at a dose of 400-mg/kg body weight, which served as standard for comparison. Group 5 to 22 received at a dose of 25 mg/kg body weight. Lesions were induced 1 hour after ethanol challenge animals. The stomach was ligated at the pylorus under ether anesthesia. 4 hours after pylorus ligation, the animals were sacrificed and the contents drained and centrifuges at 5000 rpm for 10 minutes. Aliquots of supernatant were used for determination of total acid by titrating with 0.01N NaOH using topfers reagent and phenolphthalein indicators. Results are tabulated in Table no. 3.

2.4 Pylorus Ligated Ulcers

The animals were divided into 19 groups of 6 animals each. Animals were deprived of food for 48 hours but had free access to water. Group 1 received the vehicle Tween 80 (1%, 1 ml) which served as the control. Group 2 received ranitidine at a dose of 50-mg/kg-body weight, which served as standard for comparison. Group 3 to 20 received at a dose of 25 mg/kg body weight. After one hour of administration of drug the stomach was ligated at the pylorus under ether anesthesia. 4 hours after pylorus ligation, the animals were sacrificed and the contents drained and centrifuges at 5000 rpm for 10 minutes. Aliquots of supernatant were used for determination of total acid by titrating with 0.01N NaOH using topfers reagent and phenolphthalein indicators. Results are given in table no. 4.

2.5 Acetyl Salicylic Acid Induced Ulcer:

The antiulcer activity of the compounds was studied. The animals were divided into 19 groups of 6 animals each. Group 1 received the vehicle Tween 80 (1%, 1 ml) which served as the control. Group 2 received ranitidine at a dose of 50-mg/kg-body weight, which served as standard for comparison. Group 3 to 8 at a dose of 50, 25, 15, 10 and 5 mg/kg body weight respectively. Rats were administered per orally with a daily dose of the compounds and the drug ranitidine to respective groups for a period of five days and then fasted for 24 hours. The narcotizing agent acetyl salicylic acid (aspirin) at a dose of 200 mg/kg body weight was administered as a suspension in tween-80 (1%), 30 min after the drug administration each day. All drugs were administered orally on ht e6th day after the last administration of the drugs and the ulcer inducing agent aspirin, the rats were killed by cervical dislocation and their stomach were opened along the greater curvature and washed with luke warm saline and examined under a dissecting microscope. The ulcer index was calculated for each stomach and is given in Table 5.

2.6 Cold Restraint Induced Ulcers

The antiulcer activity of the compounds was studied. The animals were divided into 8 groups of 6 animals each. Group 1 received the vehicle Tween 80 (1%, 1 ml) which served as the control. Group 2 received ranitidine at a dose of 50-mg/kg body weight, which served as standard for comparison. Group 3 to 8 at a dose of 50, 25, 15, 10 and 5 mg/kg body weight respectively. Animals were deprived of food 48 hours before the experiment. The water was allowed for free access. Rats were administered per orally with compounds and the drug ranitidine. The water was removed 1 hour before restraint and exposed to a temperature of 4° C. for 2 hours. Two hours after stress, the animals were sacrificed. The stressed animals were opened along the greater curvature and the severity of gastric ulcer was assessed in terms of mean ulcer index. Results are given in Table 6.

2.7 Ethanol Induced Ulcers

The animals were divided into 9 groups of 6 animals each. Animals were deprived of food for 48 hours but had free access to water. Group 1 received the vehicle Tween 80 (1%, 1 ml) which served as the control. Group 2 received ranitidine at a dose of 50-mg/kg-body weight, which served as standard for comparison. Group 3 to received Omeprazole at a dose of 30-mg/kg body weight, which served as standard for comparison. Group 4 received sucralfate at a dose of 400-mg/kg body weight, which served as standard for comparison. Group 5 to 9 received at a dose of 50, 25, 15, 10 and 5 mg/kg body weight respectively. Lesions were induced 1 hour after ethanol challenge animals. The stomach was ligated at the pylorus under ether anesthesia. 4 hours after pylorus ligation, the animals were sacrificed and the contents drained and centrifuges at 5000 rpm for 10 minutes. Aliquots of supernatant were used for determination of total acid by titrating with 0.01N NaOH using topfers reagent and phenolphthalein indicators. Results are given in Table 7.

2.8 Pylorus Ligated Ulcers

The animals were divided into 7 groups of 6 animals each. Animals were deprived of food for 48 hours but had free access to water. Group 1 received the vehicle Tween 80 (1%, 1 ml) which served as the control. Group 2 received ranitidine at a dose of 50-mg/kg-body weight, which served as standard for comparison. Group 3 to 7 received at a dose of 50, 25, 15, 10 and 5 mg/kg body weight respectively. After one hour of administration of drug the stomach was ligated at the pylorus under ether anesthesia. 4 hours after pylorus ligation, the animals were sacrificed and the contents drained and centrifuges at 5000 rpm for 10 minutes. Aliquots of supernatant were used for determination of total acid by titrating with 0.01N NaOH using topfers reagent and phenolphthalein indicators. Results are given in Table 8.

TABLE 1

Ulcer protective effect of samples in acetyl salicylic acid induced gastric lesions

| Group no. | No. of animals | Average weight | Treatment | Dose (mg/kg) | Ulcer index Mean(SE) | Inhibition % |
|---|---|---|---|---|---|---|
| 1 | 6 | 180 | Control | 1 ml (1%) | 45.12 (±1.82) | — |
| 2 | 6 | 180 | Ranitidine | 50 | 11.66 (±3.00) | 74.15 |
| 3 | 6 | 180 | OA-5 | 25 | 11.06 (±2.10) | 74.55 |
| 4 | 6 | 180 | Oroxylin A | 25 | 42.50 (±1.70) | 05.81 |
| 5 | 6 | 182 | Chrysin | 25 | 24.06 (±0.24) | 46.67 |
| 6 | 6 | 180 | Baicalein | 25 | 40.83 (±3.09) | 09.51 |
| 7 | 6 | 180 | Methoxy chrysin | 25 | 40.00 (±2.88) | 11.35 |
| 8 | 6 | 181 | ORC-16 | 25 | 39.13 (±3.74) | 13.27 |
| 9 | 6 | 182 | ORPM-1 | 25 | 37.49 (±3.27) | 16.91 |
| 10 | 6 | 180 | NMC-2 | 25 | 23.33 (±6.00) | 48.30 |
| 11 | 6 | 181 | NMC-3 | 25 | 30.00 (±5.62) | 33.52 |
| 12 | 6 | 180 | CHN-2 | 25 | 20.00 (±4.21) | 55.68 |
| 13 | 6 | 182 | CHM-2 | 25 | 19.99 (±6.66) | 55.59 |
| 14 | 6 | 181 | CHM-3 | 25 | 21.77 (±3.65) | 51.74 |
| 15 | 6 | 179 | CPP-2 | 25 | 14.99 (±3.07) | 66.77 |
| 16 | 6 | 180 | OA-G | 25 | 30.66 (±1.76) | 32.05 |
| 17 | 6 | 180 | OA-5 acid | 25 | 23.33 (±8.81) | 48.30 |
| 18 | 6 | 180 | CG | 25 | 21.66 (±3.33) | 52.00 |
| 19 | 6 | 181 | CGL | 25 | 13.33 (±1.66) | 70.46 |

OA-5 = Oroxyloside methyl ester (FIG.: 5)
Oroxylin A = (FIG.: 1)
Chrysin = (FIG.: 2)
Baicalein = (FIG.: 3)
Methoxy chrysin = (FIG: 4)
ORC-16 = (FIG.: 7)
ORPM-1 = (FIG.: 8)
NMC-2 = (FIG.: 12)
NMC-3 = (FIG.: 13)
CHN-2 = (FIG.: 11)
CHM-2 = (FIG.: 10)
CHM-3 = (FIG.: 14)
CPP-2 = (FIG.: 9)
OA-G = (FIG.: 15)
OA-5 acid = (FIG.: 17)
CG = (FIG.: 16)
CGL = (FIG.: 6)

TABLE 2

Effect of samples on gastric ulceration in cold restraint rats

| Group no. | No. of animals | Average weight | Treatment | Dose (mg/kg) | Ulcer index Mean (SE) | Inhibition % |
|---|---|---|---|---|---|---|
| 1 | 7 | 170 | Control | 1 ml (1%) | 40.17 (±3.99) | — |
| 2 | 7 | 170 | Ranitidine | 50 | 08.62 (±2.85) | 78.83 |
| 3 | 7 | 170 | Diazepam | 1 | 10.00 (±2.18) | 75.44 |
| 4 | 7 | 170 | OA-5 | 25 | 9.997 (±1.84) | 75.45 |
| 5 | 7 | 171 | Oroxylin A | 25 | 38.57 (±4.04) | 5.26 |
| 6 | 7 | 172 | Chrysin | 25 | 23.03 (±0.25) | 42.66 |
| 7 | 7 | 170 | Baicalein | 25 | 29.28 (±2.52) | 3.52 |
| 8 | 7 | 172 | Methoxy chrysin | 25 | 27.14 (±2.85) | 8.77 |
| 9 | 7 | 170 | ORC-16 | 25 | 35.00 (±2.43) | 14.03 |
| 10 | 7 | 171 | ORPM-1 | 25 | 22.85 (±2.85) | 24.23 |
| 11 | 7 | 170 | NMC-2 | 25 | 16.42 (±2.76) | 59.67 |
| 12 | 7 | 170 | NMC-3 | 25 | 17.13 (±3.40) | 57.92 |
| 13 | 7 | 171 | CHN-2 | 25 | 17.85 (±2.97) | 56.12 |
| 14 | 7 | 171 | CHM-2 | 25 | 26.42 (±0.92) | 35.11 |
| 15 | 7 | 170 | CHM-3 | 25 | 19.28 (±4.08) | 52.64 |
| 16 | 7 | 170 | CPP-2 | 25 | 15.71 (±2.60) | 61.44 |
| 17 | 7 | 171 | OA-G | 25 | 32.33 (±1.45) | 19.52 |
| 18 | 7 | 172 | OA-5 acid | 25 | 23.33 (±1.33) | 41.93 |
| 19 | 7 | 170 | CG | 25 | 21.00 (±2.00) | 47.73 |
| 20 | 7 | 170 | CGL | 25 | 20.00 (±1.73) | 50.22 |

TABLE 3

Ulcer protective effect of samples on ethanol induced gastric ulcers

| Group No. | No. of animals | Average weight | Treatment | Dose (mg/kg) | Gastric content | pH | Acidity Total mEg | Ulcer index Mean(SE) | Inhibition % |
|---|---|---|---|---|---|---|---|---|---|
| 1 | 6 | 190 | Control | 1 ml (1%) | 3.9 (±0.02) | 2.66 (±0.22) | 62.00 (±2.71) | 66.66 (±1.66) | — |
| 2 | 6 | 190 | Ranitidine | 50 | 5.0 (±0.48) | 4.96 (±0.13) | 26.74 (±1.54) | 25.83 (±2.22) | 61.26 |
| 3 | 6 | 190 | Omeprazole | 30 | 3.5 (±0.68) | 4.65 (±0.19) | 32.01 (±1.52) | 23.33 (±2.21) | 67.51 |
| 4 | 6 | 190 | Sucralfate | 400 | 3.01 (±0.48) | 3.00 (±0.19) | 58.00 (±2.30) | 08.33 (±2.23) | 87.50 |
| 5 | 6 | 190 | OA-5 | 25 | 5.5 (±0.30) | 6.81 (±0.26) | 12.40 (±2.30) | 11.66 (±4.47) | 82.50 |
| 6 | 6 | 191 | Oroxylin A | 25 | 4.0 (±0.45) | 3.19 (±0.73) | 48.24 (±2.84) | 48.33 (±3.33) | 27.50 |
| 7 | 6 | 190 | Chrysin | 25 | 4.20 (±0.02) | 3.20 (±0.40) | 48.00 (±2.20) | 60.66 (±2.88) | 09.01 |
| 8 | 6 | 191 | Baicalein | 25 | 3.5 (±0.20) | 3.33 (±0.10) | 45.21 (±3.10) | 43.33 (±3.33) | 20.00 |
| 9 | 6 | 192 | Methoxy chrysin | 25 | 3.9 (±0.40) | 2.91 (±0.15) | 49.20 (±4.12) | 46.66 (±1.66) | 15.01 |
| 10 | 6 | 191 | ORC-16 | 25 | 3.7 (±0.10) | 3.58 (±0.23) | 43.20 (±3.86) | 51.50 (±1.05) | 22.75 |
| 11 | 6 | 192 | ORPM-1 | 25 | 3.0 (±1.50) | 3.50 (±0.18) | 44.24 (±0.62) | 47.50 (±1.11) | 28.75 |
| 12 | 6 | 190 | NMC-2 | 25 | 4.8 (±0.06) | 4.75 (±0.28) | 30.26 (±0.42) | 28.33 (±3.33) | 57.50 |
| 13 | 6 | 189 | NMC-3 | 25 | 4.5 (±1.12) | 4.50 (±0.18) | 33.48 (±2.28) | 42.50 (±3.09) | 36.25 |
| 14 | 6 | 190 | CHN-2 | 25 | 3.2 (±0.42) | 5.14 (±0.36) | 28.10 (±0.48) | 38.33 (±3.07) | 42.50 |
| 15 | 6 | 190 | CHM-2 | 25 | 2.8 (±0.72) | 4.00 (±0.18) | 38.28 (±2.24) | 40.11 (±3.65) | 25.00 |
| 16 | 6 | 190 | CHM-3 | 25 | 3.8 (±0.30) | 4.16 (±0.12) | 37.10 (±0.60) | 42.50 (±3.81) | 36.25 |
| 17 | 6 | 190 | CPP-2 | 25 | 3.2 (±0.62) | 3.33 (±0.16) | 44.60 (±4.12) | 28.83 (±2.71) | 36.25 |
| 18 | 6 | 190 | OH-mix | 25 | 2.6 (±0.25) | 4.33 (±0.10) | 35.20 (±3.86) | 35.10 (±5.41) | 32.50 |
| 19 | 6 | 190 | OA-G | 25 | 4.33 (±0.11) | 4.31 (±0.11) | 36.66 (±0.88) | 53.33 (±6.66) | 20.00 |
| 20 | 6 | 192 | OA-5 acid | 25 | 5.50 (±0.28) | 3.20 (±0.17) | 47.66 (±1.45) | 36.66 (±3.33) | 45.01 |
| 20 | 6 | 189 | CG | 25 | 5.90 (±0.49) | 5.90 (±0.49) | 20.01 (±4.41) | 31.66 (±4.41) | 52.50 |
| 21 | 6 | 189 | CGL | 25 | 4.60 (±0.20) | 3.91 (±0.21) | 39.00 (±1.52) | 25.00 (±2.88) | 62.50 |

TABLE 4

Antisecretory and ulcer protective effect of samples in Pylorus ligated rats

| Group No. | No. of animals | Average weight (g) | Treatment | Dose (mg/kg) | Gastric content | pH | Acidity Total m Eg | Ulcer index Mean(SE) | Inhibition % |
|---|---|---|---|---|---|---|---|---|---|
| 1 | 6 | 195 | Control | 1% | 2.24 (±0.22) | 2.83 (±0.33) | 52.42 (±3.28) | 50.11 (±3.65) | — |
| 2 | 6 | 195 | Ranitidine | 50 | 1.82 (±0.44) | 4.75 (±0.22) | 31.8 (±1.91) | 10.83 (±3.21) | 78.39 |
| 3 | 6 | 196 | OA-5 | 25 | 2.10 (±0.34) | 5.62 (±0.19) | 30.18 (±0.50) | 12.49 (±3.74) | 75.07 |
| 4 | 6 | 196 | Oroxylin A | 25 | 2.30 (±0.42) | 2.74 (±0.24) | 55.24 (±2.40) | 50.80 (±2.00) | 0.00 |
| 5 | 6 | 192 | Chrysin | 25 | 1.85 (±0.82) | 4.00 (±0.40) | 56.00 (±0.82) | 37.21 (±0.26) | 25.74 |
| 6 | 6 | 195 | Baicalein | 25 | 2.00 (±0.22) | 3.01 (±0.30) | 49.21 (±2.20) | 40.66 (±5.50) | 18.86 |
|  | 6 | 195 | Methoxy chrysin | 25 | 2.20 (±0.44) | 3.20 (±0.25) | 47.20 (±2.40) | 48.80 (±3.07) | 2.62 |

TABLE 4-continued

Antisecretory and ulcer protective effect of samples in Pylorus ligated rats

| Group No. | No. of animals | Average weight (g) | Treatment | Dose (mg/kg) | Gastric content | pH | Acidity Total m Eg | Ulcer index Mean(SE) | Inhibition % |
|---|---|---|---|---|---|---|---|---|---|
| 7  | 6 | 194 | ORC-16   | 25 | 1.92 (±0.20) | 3.66 (±0.20) | 42.20 (±2.20) | 43.33 (±2.10) | 1354 |
| 8  | 6 | 195 | ORPM-1   | 25 | 2.20 (±0.22) | 3.20 (±0.25) | 45.24 (±0.30) | 41.66 (±2.78) | 16.87 |
| 9  | 6 | 195 | NMC-2    | 25 | 1.90 (±0.62) | 4.25 (±0.14) | 36.26 (±2.80) | 28.33 (±0.10) | 43.47 |
| 10 | 6 | 195 | NMC-3    | 25 | 1.92 (±0.20) | 3.54 (±0.15) | 43.48 (±2.50) | 33.33 (±2.47) | 33.49 |
| 11 | 6 | 194 | CHN-2    | 25 | 1.80 (±0.46) | 4.25 (±0.09) | 37.18 (±4.20) | 20.83 (±2.00) | 58.44 |
| 12 | 6 | 195 | CHM-2    | 25 | 1.88 (±0.62) | 3.79 (±0.20) | 41.48 (±3.20) | 25.82 (±2.00) | 48.47 |
| 13 | 6 | 196 | CHM-3    | 25 | 2.24 (±0.22) | 3.41 (±0.16) | 44.10 (±2.20) | 27.46 (±3.00) | 45.19 |
| 14 | 6 | 195 | CPP-2    | 25 | 2.60 (±0.24) | 3.25 (±0.11) | 29.06 (±2.20) | 15.80 (±2.71) | 68.47 |
| 15 | 6 | 194 | OH-mix   | 25 | 2.40 (±0.24) | 3.87 (±0.19) | 40.20 (±2.10) | 32.50 (±1.11) | 35.15 |
| 16 | 6 | 196 | OA-G     | 25 | 4..50 (±0.28) | 3.20 (±0.15) | 41.66 (±1.66) | 35.00 (±2.88) | 30.16 |
| 17 | 6 | 195 | OA-5 acid | 25 | 2.16 (±0.16) | 3.03 (±0.03) | 41.00 (±0.57) | 38.33 (±1.66) | 23.51 |
| 18 | 6 | 195 | CG       | 25 | 1.50 (±0.28) | 3.50 (±0.28) | 44.33 (±2.33) | 24.93 (±1.66) | 50.25 |
| 19 | 6 | 194 | CGL      | 25 | 4.83 (±0.44) | 3.08 (±0.22) | 40.00 (±1.15) | 19.96 (±6.66) | 60.17 |
| 20 | 6 | 192 | Chrysin  | 25 | 1.85 (±0.82) | 4.00 (±0.40) | 56.00 (±0.82) | 37.21 (±0.26) | 25.74 |

TABLE 5

Ulcer protective effect of OA - 5 in acetyl salicylic acid induced gastric lesions

| Group no. | No. of animals | Average weight | Treatment | Dose (mg/kg) | Ulcer index Mean(SE) | Inhibition % |
|---|---|---|---|---|---|---|
| 1 | 6 | 180 | Control   | 1 ml (1%) | 45.12 (±1.82) | — |
| 2 | 6 | 180 | Ranitidine | 50 | 11.66 (±3.00) | 74.15 |
| 3 | 6 | 180 | OA-5 | 50 | 10.00 (±3.50) | 77.84 |
| 4 | 6 | 180 | OA-5 | 25 | 11.06 (±2.10) | 74.55 |
| 5 | 6 | 180 | OA-5 | 15 | 26.66 (±7.20) | 40.98 |
| 6 | 6 | 180 | OA-5 | 10 | 26.66 (±4.70) | 40.98 |
| 7 | 6 | 181 | OA-5 | 5  | 36.66 (±2.72) | 18.75 |

TABLE 6

Effect of OA - 5 on gastric ulceration in cold restraint rats

| Group no. | No. of animals | Average weight | Treatment | Dose (mg/kg) | Ulcer index Mean(SE) | Inhibition % |
|---|---|---|---|---|---|---|
| 1 | 6 | 170 | Control    | 1 ml (1%) | 40.17 (±3.99) | — |
| 2 | 6 | 170 | Ranitidine | 50 | 08.62 (±2.85) | 78.83 |
| 3 | 6 | 170 | Diazepam   | 1  | 10.00 (±2.18) | 75.44 |
| 4 | 6 | 170 | OA-5 | 50 | 8.75 (±2.16) | 78.22 |
| 5 | 6 | 170 | OA-5 | 25 | 9.99 (±1.84) | 75.45 |
| 6 | 6 | 170 | OA-5 | 15 | 19.99 (±5.4) | 50.14 |
| 7 | 6 | 172 | OA-5 | 10 | 23.33 (±4.74) | 41.92 |
| 8 | 6 | 171 | OA-5 | 5  | 27.5 (±4.14) | 31.55 |

TABLE 7

Ulcer protective effect of OA - 5 on ethanol induced gastric ulcers

| Group no. | No. of animals | Average weight | Treatment | Dose (mg/kg) | Gastric content | pH | Acidity Total m Eg | Ulcer index Mean(SE) | Inhibition % |
|---|---|---|---|---|---|---|---|---|---|
| 1 | 6 | 190 | Control    | 1 ml (1%) | 3.9 (±0.02) | 2.66 (±0.22) | 62.00 (±2.71) | 66.66 (±1.66) | — |
| 2 | 6 | 190 | Ranitidine | 50  | 5.0 (±0.48) | 4.96 (±0.13) | 26.74 (±1.54) | 25.83 (±2.22) | 61.26 |
| 3 | 6 | 190 | Omeprazole | 30  | 3.5 (±0.68) | 4.65 (±0.19) | 26.01 (±1.52) | 23.33 (±2.21) | 67.51 |
| 4 | 6 | 190 | Sucralfate | 400 | 3.0 (±0.48) | 3.00 (±0.19) | 58.00 (±2.30) | 08.33 (±2.23) | 87.50 |
| 5 | 6 | 190 | OA-5 | 50 | 7.4 (±0.72) | 4.95 (±0.43) | 18.25 (±7.10) | 10.00 (±6.23) | 85.00 |
| 6 | 6 | 191 | OA-5 | 25 | 5.5 (±0.30) | 6.81 (±0.26) | 12.40 (±2.30) | 11.66 (±4.47) | 82.50 |
| 7 | 6 | 192 | OA-5 | 15 | 4.0 (±0.82) | 4.5 (±0.13) | 29.66 (±1.36) | 26.66 (±4.71) | 60.61 |
| 8 | 6 | 191 | OA-5 | 10 | 4.2 (±0.07) | 4.66 ± (0.13) | 31.33 (±1.36) | 43.33 (±5.40) | 35.00 |
| 9 | 6 | 191 | OA-5 | 5  | 4.0 (±0.45) | 3.5 (±0.40) | 42.66 (±3.95) | 46.66 (±0.80) | 30.01 |

TABLE 8

Antisecretory and ulcer protective effect of OA - 5 in Pylorus ligated rats

| Group no. | No. of animals | Average weight (g) | Treatment | Dose (mg/kg) | Gastric content | pH | Acidity Total mEg | Ulcer index Mean(SE) | Inhibition % |
|---|---|---|---|---|---|---|---|---|---|
| 1 | 6 | 190 | Control | 1% | 2.24 (±0.22) | 2.83 (±0.33) | 52.42 (±3.28) | 50.11 (±3.65) | — |
| 2 | 6 | 190 | Ranitidine | 50 | 1.82 (±0.44) | 4.75 (±0.22) | 31.8 (±1.91) | 10.83 (±3.21) | 78.39 |
| 3 | 6 | 190 | OA-5 | 50 | 2.50 (±0.19) | 4.62 (±0.10) | 32.66 (±0.62) | 10.10 (±2.04) | 79.85 |
| 4 | 6 | 191 | OA-5 | 25 | 2.10 (±0.34) | 5.62 (±0.19) | 30.18 (±0.50) | 12.49 (±3.74) | 75.07 |
| 5 | 6 | 192 | OA-5 | 15 | 3.62 (±0.61) | 4.35 (±0.10) | 30.25 (±0.73) | 15.00 (±3.33) | 70.07 |
| 6 | 6 | 190 | OA-5 | 10 | 3.50 (±0.62) | 3.58 (±0.24) | 42.90 (±2.37) | 21.66 (±3.04) | 59.78 |
| 7 | 6 | 189 | OA-5 | 5 | 2.06 (±0.28) | 3.25 (±0.17) | 45.50 (±1.25) | 26.66 (±5.48) | 46.80 |

We claim:

1. A method for treating gastric ulcers induced by aspirin, the method comprising administering to a subject in need thereof a pharmaceutically effective amount of a compound selected the group consisting of:

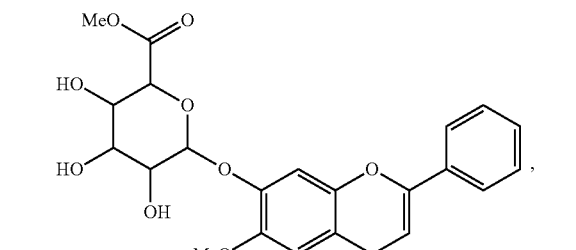

,

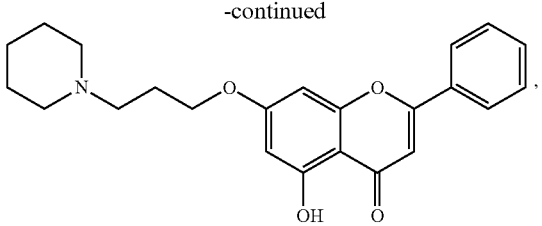

,

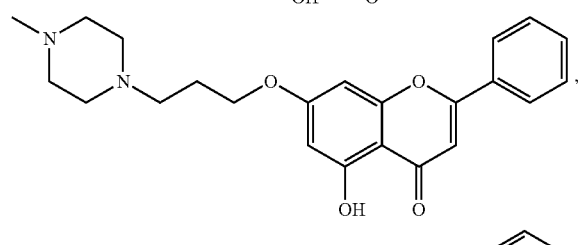

,

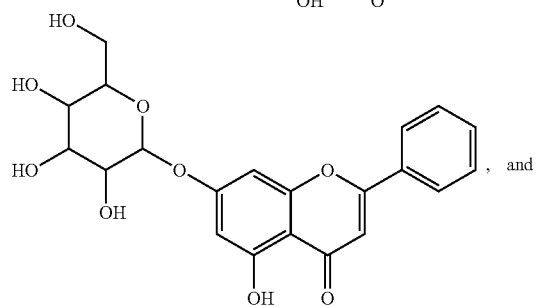

,

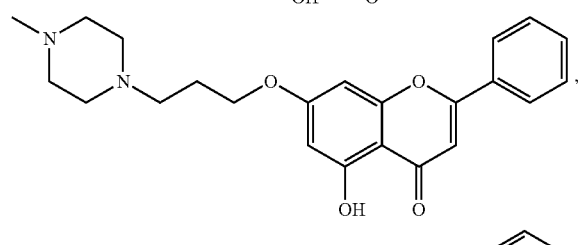

,

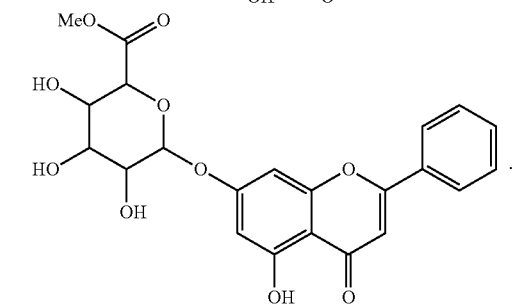

, and

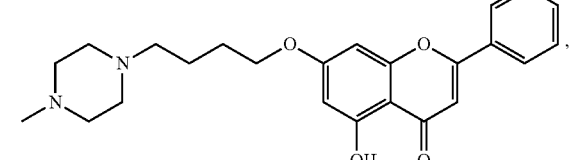

,

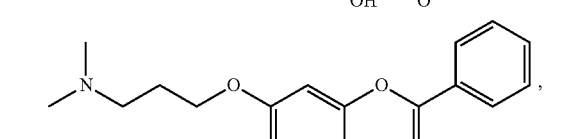

.

2. The method of claim 1, wherein

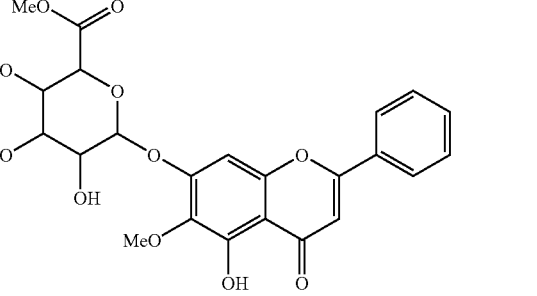

provides mucoprotective property up to 77.84% induced by aspirin at dose level of 50 mg/kg of bodyweight in comparison with reference standard ranitidine up to 74.15% protective at dose level of 50 mg/kg of bodyweight.

3. The method of claim 1, wherein,

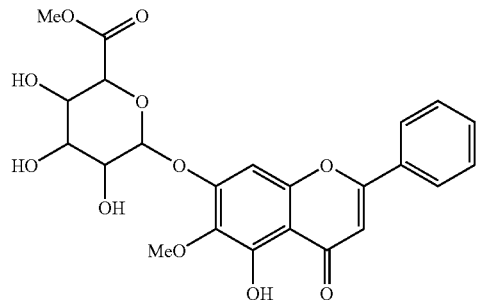

provides mucoprotective property up to 74.55% induced by aspirin at dose level of 25 mg/kg of bodyweight in comparison with reference standard ranitidine up to 74.15% protective at dose level of 50 mg/kg of bodyweight.

4. The method of claim 1, wherein,

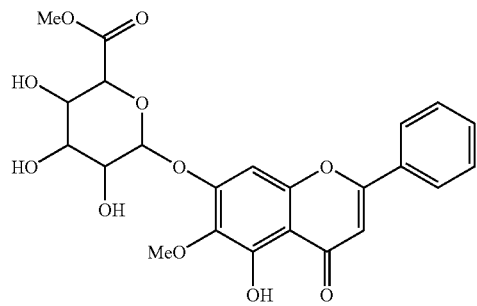

provides mucoprotective property up to 40.98% induced by aspirin at dose level of 15 mg/kg of bodyweight in comparison with reference standard ranitidine up to 74.15% protective at dose level of 50 mg/kg of bodyweight.

5. The method of claim 1, wherein,

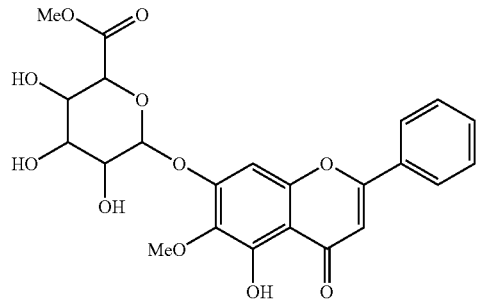

provides mucoprotective property up to 40.98% induced by aspirin at dose level of 10 mg/kg of bodyweight in comparison with reference standard ranitidine up to 74.15% protective at dose level of 50 mg/kg of bodyweight.

6. The method of claim 1, wherein,

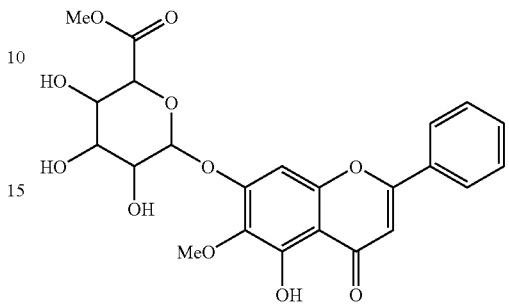

provides mucoprotective property up to 18.75% induced by aspirin at dose level of 5 mg/kg of bodyweight in comparison with reference standard ranitidine up to 74.15% protective at dose level of 50 mg/kg of bodyweight.

7. The method of claim 1 wherein,

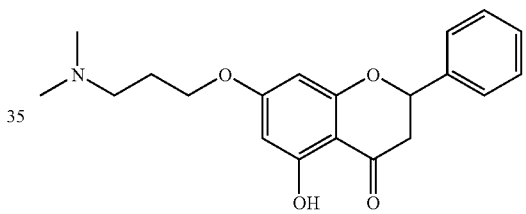

provides mucoprotective property up to 55.68% induced by aspirin at dose level of 25 mg/kg of bodyweight in comparison with reference standard ranitidine up to 74.15% protective at dose level of 50 mg/kg of bodyweight.

8. The method of claim 1 wherein,

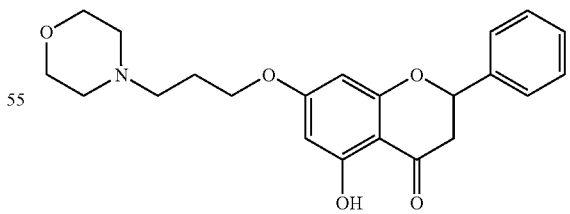

provides mucoprotective property up to 55.59% induced by aspirin at dose level of 25 mg/kg of bodyweight in comparison with reference standard ranitidine up to 74.15% protective at dose level of 50 mg/kg of bodyweight.

9. The method of claim 1 wherein,

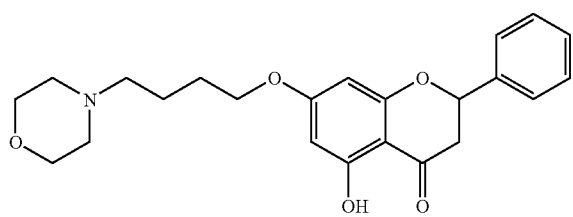

provides mucoprotective property up to 51.74% induced by aspirin at dose level of 25 mg/kg of bodyweight in comparison with reference standard ranitidine up to 74.15% protective at dose level of 50 mg/kg of bodyweight.

10. The method of claim 1 wherein,

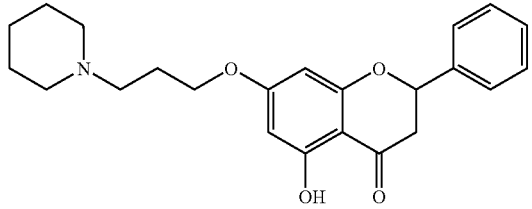

provides mucoprotective property up to 66.77% induced by aspirin at dose level of 25 mg/kg of bodyweight in comparison with reference standard ranitidine up to 74.15% protective at dose level of 50 mg/kg of bodyweight.

11. The method of claim 1, wherein,

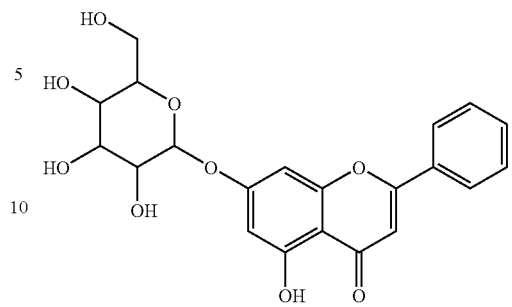

provides mucoprotective property up to 52% induced by aspirin at dose level of 25 mg/kg of bodyweight in comparison with reference standard ranitidine up to 74.15% protective at dose level of 50 mg/kg of bodyweight.

12. The method of claim 1, wherein,

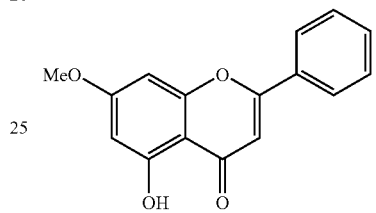

provides mucoprotective property up to 70.46% induced by aspirin at dose level of 25 mg/kg of bodyweight in comparison with reference standard ranitidine up to 74.15% protective at dose level of 50 mg/kg of bodyweight.

13. The method of claim 1, wherein the compound is isolated from *Oroxylum indicum*.

* * * * *